US007605241B2

(12) United States Patent
Hecht et al.

(10) Patent No.: US 7,605,241 B2
(45) Date of Patent: Oct. 20, 2009

(54) SYNTHESIS OF INHIBITORS OF P90RSK

(75) Inventors: Sidney M. Hecht, Charlottesville, VA (US); David J. Maloney, New York, NY (US)

(73) Assignee: University of Virginia Patent Foundation, Charlottesville, VA (US)

( * ) Notice: Subject to any disclaimer, the term of this patent is extended or adjusted under 35 U.S.C. 154(b) by 104 days.

(21) Appl. No.: 11/794,969

(22) PCT Filed: Jan. 10, 2006

(86) PCT No.: PCT/US2006/000709

§ 371 (c)(1),
(2), (4) Date: Jul. 10, 2007

(87) PCT Pub. No.: WO2006/086103

PCT Pub. Date: Aug. 17, 2006

(65) Prior Publication Data

US 2008/0269144 A1    Oct. 30, 2008

Related U.S. Application Data

(60) Provisional application No. 60/642,539, filed on Jan. 10, 2005.

(51) Int. Cl.
*C07G 3/00* (2006.01)
*C07H 17/00* (2006.01)
(52) U.S. Cl. .................. 536/18.5; 536/18.6; 536/124
(58) Field of Classification Search .................. None
See application file for complete search history.

(56) References Cited

U.S. PATENT DOCUMENTS

| | | | |
|---|---|---|---|
| 4,559,157 | A | 12/1985 | Smith et al. |
| 4,608,392 | A | 8/1986 | Jacquet et al. |
| 4,820,508 | A | 4/1989 | Wortzman |
| 4,938,949 | A | 7/1990 | Borch et al. |
| 4,992,478 | A | 2/1991 | Geria |

FOREIGN PATENT DOCUMENTS

| | | |
|---|---|---|
| WO | WO03/105766 | 12/2003 |
| WO | WO 03/105766 | * 12/2003 |

OTHER PUBLICATIONS

Maloney et al., "Synthesis of a Potent and Selective Inhibitor of p90 Rsk", Organic Letters, 2005, vol. 7(6), 1097-99.*
International Search Report for PCT/US2006/00709 mailed Aug. 2, 2006.
Adam, Waldemar, et al., "Spectral And Chemical Properties Of Dimethyldioxirane As Determined By Experiement And ab Initio Calculations", 1987, *Journal Organic Chemistry*, vol. 52, pp. 2800-2803.
Adam, Waldemar, et al., "Dioxirane Epoxidation Of α,β-Unsaturated Ketones", 1990, *Chem. Ber.*, vol. 124, pp. 227-232.
Adam, Waldemar, et al., "Epoxidation of Flavones by Dimethyldioxirane", 1991, *Journal of Organic Chemistry*, vol. 56, pp. 7292-7297.
Bang, Yung-Jue, et al., "Increased MAPK Activity and MKP-1 Overexpression in Human Gastric Adenocarcinoma", 1998, *Biochemical and Biophysical, Research Communications*, vol. 250, No. 1, pp. 43-47.
Bashir, Nazir B., et al., "Enzymatic Esterification And De-Esterification Of Carbohydrates: Synthesis Of A Naturally Occuring Rhamnopyranoside of *p*-Hydroxy-Benzaldehyde And A Systematic Investigation Of Lipase-Catalysed Acylation Of Seclected Arylpyranosides", 1995, *Journal Chem. Soc.*, pp. 2203-2222.
Bokemeyer, Dirk, et al., "In Vivo Identification Of The Mitogen-Activated Protein Kinase Cascade As A Central Pathogenic Pathway In Experimental Mesangioproliferative Glomerulonephritis", 2002, *Journal of the American Society of Nephrology*, No. 13, pp. 1473-1480.
Cobb, Melanie H., "MAP Kinase Pathways", 1999, *Progress In Biophysics & Molecular Biology*, vol. 71, pp. 479-500.
Crich, David, et al., "The 3,4-O-Carbonate Protecting Group as a β-Directing Group In Rhamnopyranosylation In Both Homogeneous And Heterogeneous Glycosylations As Compared To The Chameleon-Like 2,3-O-Carbonates", 2003, *Journal of Organic Chemistry*, vol. 68, No. 22, pp. 8453-8458.
Dai, Jin-Rui, et al., "Zerumbone, An Hiv-Inhibitory And Cytotoxic Sesquiterpene Of *Zingiber aromaticum* And *Z. zerumbet*", 1997, *Natural Products Letters*, vol. 10, pp. 115-118.
Dineley, Kelly T., et al., "β-Amyloid Activates The Mitogen-Activated Protein Kinase Cascade Via Hippocampal α7 Nicotinic Acetylocholine Receptors: In Vitro And In Vivo Mechanisms Related To Alzeheimers Disease", 2001, *The Journal of Neuroscience*, vol. 21, No. 12, pp. 4125-4133.
Demetzos, Costas, et al., "Phase-Transfer-Catalyzed Synthesis Of Flavonoid Glycosides", 1990, *Carbohydrate Research*, vol. 207, pp. 131-137.
Gomez-Santos, Cristina, et al., "Mpp Increases α-Synuclein Expression And ERK/MAP-Kinase Phosphorylation In Human Neuroblastoma SH-SY5Y Cells", 2002, *Brain Research*, No. 935, pp. 32-39.
Gonzalez, Fernando A., et al., "Identification Of Substrate Recognition Determinants For Human ERK1 And ERK2 Protein Kinases", 1991, *The Journal of Biological Chemistry*, vol. 256, No. 33, pp. 22159-22163.
Groneberg, R.D., et al., "Total Synthesis Of Calicheamicin γ$I^1$ 1. Synthesis Of The Oligosaccharide Fragment[1]", 1993, *Journal American Chemical Society*, vol. 115, pp. 7593-7611.

(Continued)

*Primary Examiner*—Traviss C McIntosh, III
(74) *Attorney, Agent, or Firm*—Barnes & Thornburg LLP

(57) ABSTRACT

The synthesis of the naturally occurring kaempferol glycoside SL0101-1, as well as analogs thereof, has been accomplished, as has its biochemical evaluation. SL0101-1 exhibits selective and potent p90 Rsk inhibitory activity at nanomolar concentrations without inhibiting the function of upstream kinases such as MEK, Raf, or PKC. The synthetic scheme of the invention verified the structural assignment of the natural product and has provided access to material sufficient for detailed biological evaluation.

6 Claims, No Drawings

OTHER PUBLICATIONS

Gura, Trisha, "Cancer Models: Systems For Identifying New Drugs Are Often Faulty", Nov. 1997, *Science 7*, vol. 278, No. 5340, pp. 1041-1042.

Hayashi, Masaaki, et al., "Big Mitogen-Activated Protein Kinase 1/Extracellular Signal-Regulated Kinase 5 Signaling Pathway Is Essential For Tumor-Associated Angiogenesis", 2005, *Cancer Research*, vol. 65, No. 17, pp. 7699-7706.

Henrich, Lorin M., et al., "Extracellular Singal-Regulated Kinase 7, A Regulator Of Hormone-Dependent Estrogen Receptor Destruction", 2003, *Mollecular and Cellular Biology*, vol. 23, No. 7, pp. 5979-5988.

Hu, Yanhua, et al., "Hyperexpression And Activation Of Extracellular Signal-Regulated Kinase (ERK1/2) In Atherosclerotic Lesions Of Cholesterol-Fed Rabbits", 2000, *American Heart Association*, vol. 20, pp. 18-26.

Inoue, A., et al., "Development Of cDNA Microarray For Expression Profiling Of Estrogen-Responsive Genes", 2002, *Journal of Molecular Endocrinology*, vol. 29, pp. 175-192.

Jackson, Mark W., et al., "Hdm2 Nuclear Export, Regulated By Insulin-Like Growth Factor-I/Mapk/P90rsk Signaling Mediates The Transformation Of Human Cells", 2006, *The Journal of Biological Chemistry*, vol. 281, No. 24, pp. 16814-16820.

Janes, Peter W., et al., "Activation Of The Ras Signalling Pathway In Human Breast Cancer Cells Overexpressing *erb*B-2", 1994, *Oncogene*, pp. 3601-3608.

Ji, Ru-Rong, et al., "ERK MAP Kinase Activation In Superficial Spinal Cord Neurons Induces Prodynophin And NK-1 Upregulation And Contributes To Persistent Inflammatory Pain Hypersensitivity", 2002, *The Journal of Neuroscience*, vol. 22, No. 2, pp. 478-485.

Katayama, Kazuhiro, et al., "Inhibition Of The Mitogen-Activated Protein Kinase Pathway Results In The Down-Reguation Of P-Glycoprotein", 2007, *Mol. Cancer Ther.*, vol. 6, No. 7, pp. 2092-2102.

Khan, M. S. Y., et al., "Synthesis Of New α-Pyronoflavones And Related Products: Part II", 1993, *Indian Journal of Chemistry*, vol. 32B, pp. 817-821.

Kitagawa, Masayuki, et al., "Arylozyacetic Acid Diuretics With Uricosuric Activity. II. Substituted [(4-Oxo-4*H*-1-Benzopyran-7-yl)oxy]acetic Acids And The Related Compounds", 1991, *Chem. Pharm. Bull.*, vol. 39, No. 10, pp. 2681-2690.

Kolch, Walter, "Meaningful Relationships: The Regulation Of The Ras/Raf/MEK/ERK Pathway By Protein Interactions", 2000, *Biochem. J.* vol. 351, pp. 289-305.

Kulich, Scott M., et al., "Sustained Extracellular Signal-Regulated Kinase Activation By 6-Hydroxydopamine: Implications For Parkinson's Disease", 2001, *Journal of Neurochemistry*, No. 77, pp. 1058-1066.

Kurokawa, Hirokazu, et al., "Inhibition Of HER2/neu (*erb*B-2) And Mitogen-Activated Protein Kinases Enhances Tamoxifen Action Against HER2-Overexpressing, Tamoxifen-Resistant Breast Cancer Cells", *Cancer Research*, vol. 60, pp. 5887-5894.

Lee, Yean-Jang, et al., "Total Synthesis Of Kaempferol And Methylated Kaempferol Derivatives", 2001, *Journal Of the Chinese Chemical Society*, vol. 48, No. 2, pp. 201-206.

Lewis, Timothy S., et al., "Signal Transduction Through MAP Kinase Cascades", 1998, *Advances in Cancer Research*, pp. 49-139.

Lu, Hailing, et al., "Inorganic Lead Activates The Mitogen-Activated Protein Kinase Kinase-Mitogen-Activated Protein Kinase-p90$^{RSK}$ Signaling Pathway In Human Astrocytoma Cells Via A Protein Kinase C-Dependent Mechanism", 2002, *The Journal of Pharmacology and Experimental Therapeutics*, vol. 300, No. 3, pp. 818-823.

Maloney, David J. "Synthesis And Biologically Active Phenolic Natural Products", 2000, *Dissertation form the Departments of Chemistry and Biology*, University of Virginia, pp. 3-6.

Matthes, H.W., et al., "Cytotoxic Components Of *Zingiber zerumbetCurcuma zedoaria* And *C. domestica*", 1980, *Phytochemistry*, vol. 19, pp. 2643-2650.

McManus, Michael, et al., "Gene Silencing In Mammals By Small Interfering RNAs", 2002, *Nature Reviews Genetics*, vol. 3, pp. 737-747.

Murray, Robert W., et al., "Chemistry Of Dioxiranes. 6. Electronic Effects In The Oxidatin Of Sulfides And Sulfoxides By Dimethyldioxirane", 1987, *Journal Organic Chemistry*, vol. 52, pp. 746-748.

Naik, Harmesh R., et al., "An In Vitro and In Vivo Study Of Antitumor Effects Of Genistein On Hormone Refractory Prostate Cancer", 1994, *Anticancer*, No. 14, pp. 2617-2619.

Nebreda, Angel R., et al., "Signal Transduction: Cell Survival Demands Some Risk", 1999, *Science*, vol. 286, No. 5443, pp. 1309-1310.

Opavsky, Mary Anne, et al., "Enhanced ERK-1/2 Activation In Mice Susceptible To Coxsackievirus-Induced Myocarditis", 2002, *The Journal of Clinical Investigation*, vol. 109, No. 12, pp. 1561-1569.

Pahl, Andreas, et al., "Regulation Of Il-13 Synthesis In Human Lymphocytes: Implications For Asthma Therapy", 2002, *British Journal of Pharmacology*, vol. 135, pp. 1915-1926.

Planz, Oliver, et al., "MEK-Specific Inhibitor U0126 Blocks Spread Of Borna Disease Virus In Cultured Cells", 2001, *Journal of Virology*, vol. 75, No. 10, pp. 4871-4877.

Pozsgay, Vince, "A Simple Method For Avoiding Alkylthio Group Migration During The Synthesis Of Thioglycoside 2,3-Orthoesters. An Improved Synthesis Of Partially Acylated 1-Thio-ά-$_L$-Ramnopyranosides", 1992, *Carbohydrate Research*, vol. 235, pp. 295-302.

Schmidt, Max, et al., "Increased MAPK Expression And Activity In Primary Human Hepatocellular Carcinoma", 1997, *Biochemical and Biophysical Research Communications*, vol. 236, pp. 54-58.

Slomiany, Bronislaw, et al., "Disruption In Gastric Mucin Synthesis By Helicobacter Pylori Lipopolysaccharide Involves ERK And p38 Mitogen-Activated Protein Kinase Participation", 2002, *Biochemical and Biophysical Research Communications*, vol. 294, pp. 220-224.

Takeishi, Yasuchika, et al., "Activation Of Mitogen-Activated Protein Kinases And p90 Ribosomal S6 Kinase In Failing Human Hearts With Dilated Cardiomyopathy", 2002, *Cardiovascular Research*, vol. 53, pp. 131-137.

Valjent, Emmanuel, et al., "Involvement Of The Extracellular Signal-Regulated Kinase Cascade For Cocaine-Rewarding Properties", 2000, *The Journal Of Neuroscience*, vol. 20, No. 23, pp. 8701-8709.

Yntema, Helger G., et al., "A Novel Ribosomal S6-Kinase (RSK4: RPS6KA6) Is Commonly Deleted In Patients With Complex X-Linked Mental Retardation", 1999, *Genomics*, vol. 62, pp. 332-343.

Zhu, Xiongwei, et al., "Differential Activation Of Neuronal ERK, JNK/SAPK And p38 In Alzheimer Disease: The 'Two Hit' Hypothesis", 2001, *Mechanisms Of Aging And Development*, vol. 123, pp. 39-46.

\* cited by examiner

SYNTHESIS OF INHIBITORS OF P90RSK

CROSS REFERENCE TO RELATED APPLICATIONS

This application is a national stage filing of International Application No. PCT/US2006/000709, filed on Jan. 10, 2006, which claims priority under 35 U.S.C. §119(e) to U.S. Provisional Application Ser. No. 60/642,539 filed Jan. 10, 2005, the disclosures of which are incorporated in their entirety herein by reference.

REFERENCE TO GOVERNMENT GRANT

This invention was supported in part by NIH Research Grant Calif. 50771. The U.S. Government may therefore have certain rights in this invention.

FIELD OF THE INVENTION

The invention relates to methods of preparing and using compounds which are inhibitors of p90Rsk.

BACKGROUND

Rsks are a family of 90 kDa ribosomal S6 kinases, which are downstream effectors of MAPK; to date four isoforms have been identified.[3] Recent studies have demonstrated the role of Rsk in cell survival signaling via the phosphorylation and inactivation of the pro-apoptotic protein BAD. Rsk has also been shown to directly promote cell survival by regulating the expression and activation of pro-survival proteins such as CREB (cyclic adenosine monophosphate response element binding protein).[4] The combination of promoting cell survival and prevention of apoptosis causes excessive cell survival, eventually leading to diseases such as cancer and autoimmune disorders. Additionally, it has been found that Rsk2 is overexpressed in more than 50% of human breast cancers, validating the Rsk family as a potential target for drug design.

The overexpression of proteins in the mitogen-activated protein kinase (MAPK) pathway has been noted for a number of human malignancies,[1] suggesting the possible utility of inhibitors of these proteins in cancer therapy. However, MAPK is involved in many fundamental cellular processes such as apoptosis, survival, differentiation, and proliferation.[2] Consequently, the inhibition of protein mediators involved in multiple processes may result in effects on both normal and cancer cells in a nonselective manner. Logically, the identification of downstream mediators in the MAPK pathway essential for tumor growth might lead to inhibitors capable of selectively targeting cancer cells.

There is a long felt need in the art for methods of preparing and using inhibitors of p90Rsk which are useful for regulating cell proliferation and treating cancer. The present invention satisfies these needs.

SUMMARY OF TILE INVENTION

Kaempferol glycosides, isolated from a methanol extract of Forsteronia refracta, that selectively inhibit p90 Rsk, have been recently described.[5] The general structure of the compound is provided below as formula I. Interestingly, in that study by Smith et al. SL-0101-1 (1) inhibited Rsk1 and Rsk2 to a greater extent than Rsk3 in spite of the fact that Rsk2 and Rsk3 are 80% homologous at the level of primary sequence. Further, in comparison to its potent inhibition of Rsk2 ($IC_{50}$ ~89 nM), 1 was found not to inhibit upstream kinases such as MEK, Raf and PKC.[5] The interesting biological activities of 1,[5] and its limited availability from natural sources, prompted an investigation into the synthesis of 1.

The present invention provides a synthetic scheme for the preparation of analogs, isomers, and derivatives of compounds having the general structure of formula I, wherein said compounds have p90 Rsk inhibitory activity. Formula I comprises:

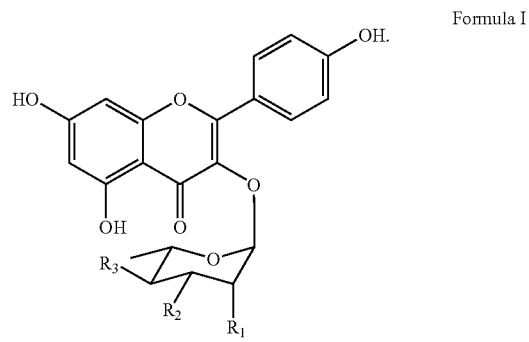

Formula I

The invention further provides synthetic schemes for preparing compounds having the general structure of formula I, wherein $R_1$ and $R_2$ are each independently selected from the group consisting of OH and OAc, and $R_3$ is OAc.

In one aspect, the present invention provides a synthetic scheme for the preparation of the compound SL-0101-1 (1) and analog, isomers, and derivatives thereof. SL-0101-1 has the general structure of formula I:

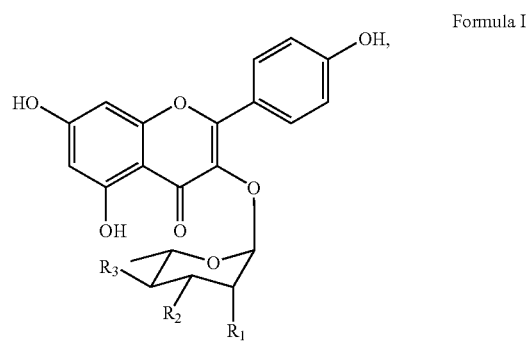

Formula I wherein, $R_1$ is OH, $R_2$ is OAc, and $R_3$ is OAc.

In one embodiment, the general scheme for synthesizing SL-0101-1 is:

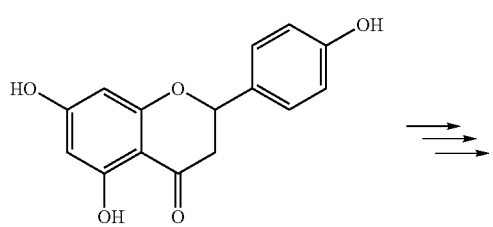

-continued

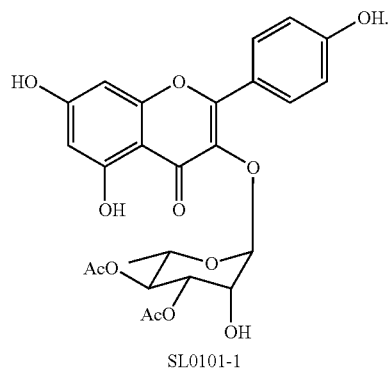
SL0101-1

In one embodiment, the synthetic scheme for compounds of the invention comprises schemes 1, 2, and 3 as disclosed in the examples. One of ordinary skill in the art would appreciate that these schemes can be modified to obtain various analogs, derivatives, and isomers of SL0101.

The present invention provides a method for synthesizing a compound with 90 kDa ribosomal S6 kinase inhibitory having the general structure of formula I:

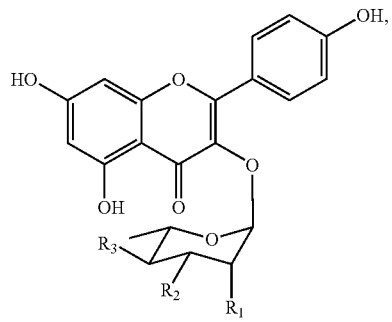

wherein $R_1$ and $R_2$ are each independently selected from the group consisting of OH and OAc, and $R_3$ is OAc:

said method comprising synthesizing from naringenin a flavonol (4),

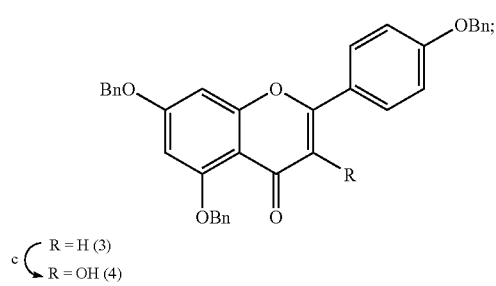

synthesizing a carbohydrate moiety by synthesizing from L-rhamnose compound 5

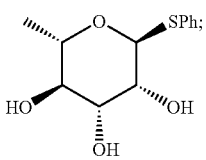

and then synthesizing rhamnosyl bromide from compound 5, followed by condensing 4 and the rhamnosyl bromide.

The invention further provides synthetic schemes 1, 2, and 3 for preparing the intermediates and compounds of the invention wherein synthetic scheme 1 comprises the following steps;

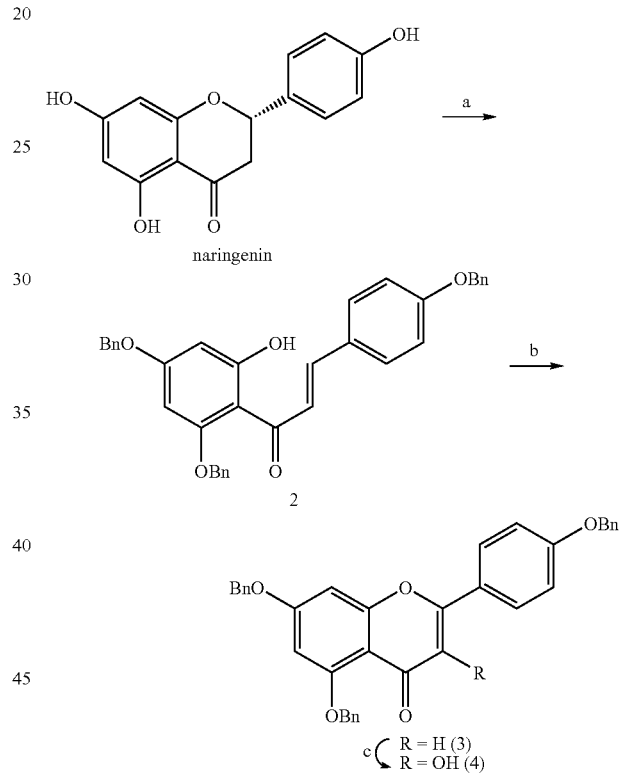

wherein the conditions for step a comprise BnBr, $K_2CO_3$, acetone, reflux, (81%)

wherein the conditions for step b comprise cat. 12, DMSO, 140° C., (72%), wherein the conditions for step c comprise DMDO, acetone, $CH_2Cl_2$, 0° C., then pTsOH, $CHCl_3$, (78%);

wherein synthetic scheme 2 comprises the following steps;

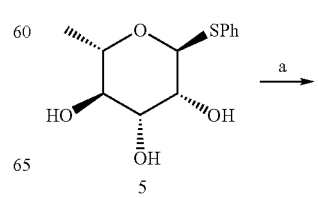

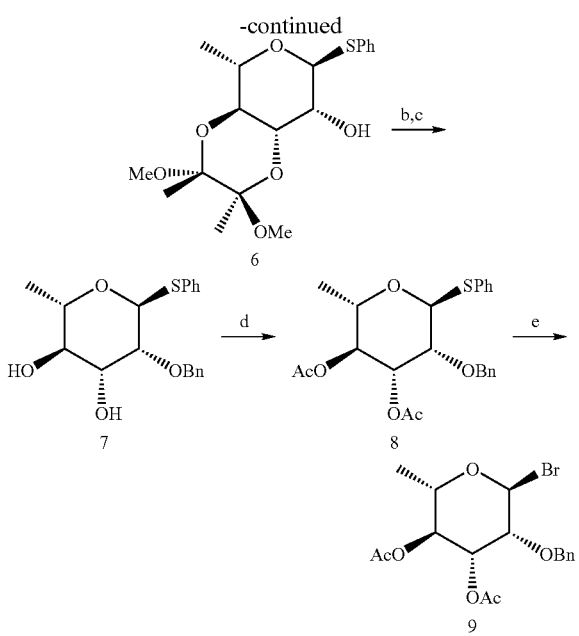

wherein the conditions for step a comprise 2,3 butanedione, CH(OMe)$_3$, cat. CSA, MeOH, reflux, (89%);

wherein the conditions for step b comprises BnBr, NaH, THF, reflux, (85%);

wherein the conditions for step c comprise TFA:H$_2$O (20:2), CH$_2$Cl$_2$, (93%);

wherein the condition for step d comprise Ac$_2$O, NEt$_3$, cat. DMAP, CH$_2$Cl$_2$, (100%);

wherein the conditions for step e comprise Br$_2$, CH$_2$Cl$_2$, 0° C., (84%); and wherein synthetic scheme 3 comprises the following steps;

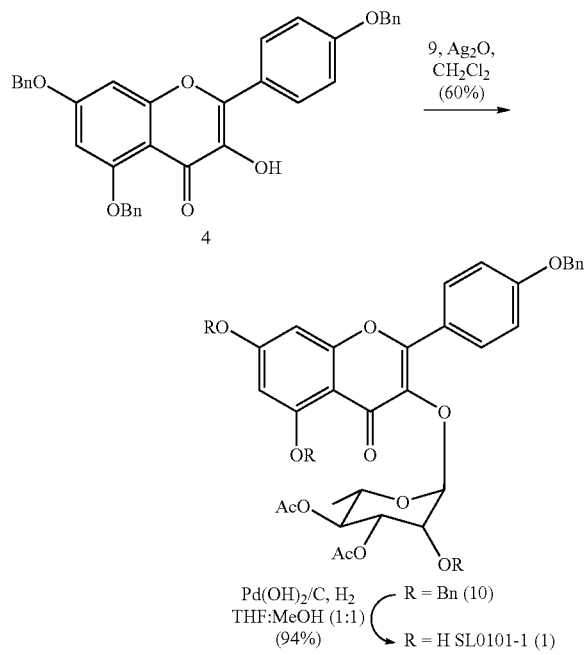

In one aspect, R$_1$ is OH and R$_2$ is OAc. In another aspect, R$_1$ is OH and R$_2$ is OH. In yet another aspect, R$_1$ is OAc and R$_2$ is OH.

The invention further provides compounds prepared by the methods of the invention.

In one embodiment, a compound of the invention inhibits cell proliferation. In one aspect, the cell is a cancer cell. In another aspect, the cancer cell is a breast cancer cell.

In one embodiment, a compound of the invention enhances cell death. In one aspect, the cell is a cancer cell. In another aspect, the cancer cell is a breast cancer cell.

The invention provides methods of treating cancer in subjects in need thereof by administering a pharmaceutical composition comprising an effective amount of a compound of the invention. The invention further provides kits for administering a compound of the invention to a subject.

Methods for testing the ability of SL0101, and analogs and derivatives thereof, synthesized according to the methods disclosed herein, to inhibit p90 ribosomal S6 kinase (RSK) activity and cellular and metabolic processes downstream from RSK activity, are known to those of ordinary skill in the art. Some specific assays are provided in citation number 5 (Smith et al., Cancer Res., 2005, 65:1027), which is incorporated by reference in its entirety. The assays include various kinase assays, cell cycle analysis, gene silencing, and analysis of cells and tissues in vitro and in vivo.

In one embodiment, the compounds are antitumor agents. In one aspect, the antitumor agents are inhibitors of p90Rsk. Also provided is a method to prepare structural analogues and derivatives of the inhibitors of p90Rsk.

Other aspects and advantages of the present invention are described herein and in the following detailed description of the embodiments thereof.

DETAILED DESCRIPTION

Abbreviations

CREB—cyclic adenosine monophosphate response element binding protein
MAPK—mitogen-activated protein kinase
RSK—a 90 kDa ribosomal S6 kinase, also referred to as p90Rsk herein Definitions Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the following terms has the meaning associated with it in this section.

The articles "a" and "an" are used herein to refer to one or to more than one (i.e. to at least one) of the grammatical object of the article. By way of example, "an element" means one element or more than one element.

As used herein, the term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

A disease or disorder is "alleviated" if the severity of a symptom of the disease or disorder, the frequency with which such a symptom is experienced by a patient, or both, are reduced.

As used herein, "amino acids" are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

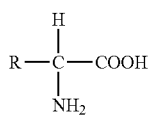

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group.

The nomenclature used to describe the peptide compounds of the present invention follows the conventional practice wherein the amino group is presented to the left and the carboxy group to the right of each amino acid residue. In the formulae representing selected specific embodiments of the present invention, the amino- and carboxy-terminal groups, although not specifically shown, will be understood to be in the form they would assume at physiologic pH values, unless otherwise specified.

As used herein, an "analog" of a chemical compound is a compound that, by way of example, resembles another in structure but is not necessarily an isomer (e.g., 5-fluorouracil is an analog of thymine).

The term "cancer" as used herein is defined as proliferation of cells whose unique trait—loss of normal controls—results in unregulated growth, lack of differentiation, local tissue invasion, and metastasis. Examples include but are not limited to, breast cancer, prostate cancer, ovarian cancer, cervical cancer, skin cancer, pancreatic cancer, colorectal cancer, renal cancer and lung cancer.

The terms "cell," "cell line," and "cell culture" as used herein may be used interchangeably. All of these terms also include their progeny, which are any and all subsequent generations. It is understood that all progeny may not be identical due to deliberate or inadvertent mutations.

A "control" cell, tissue, sample, or subject is a cell, tissue, sample, or subject of the same type as a test cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. The control may also be obtained from another source or similar source other than the test group or a test subject, where the test sample is obtained from a subject suspected of having a disease or disorder for which the test is being performed.

A "test" cell, tissue, sample, or subject is one being examined or treated.

A "pathoindicative" cell, tissue, or sample is one which, when present, is an indication that the animal in which the cell, tissue, or sample is located (or from which the tissue was obtained) is afflicted with a disease or disorder. By way of example, the presence of one or more breast cells in a lung tissue of an animal is an indication that the animal is afflicted with metastatic breast cancer.

A tissue "normally comprises" a cell if one or more of the cell are present in the tissue in an animal not afflicted with a disease or disorder.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, an "effective amount" means an amount sufficient to produce a selected effect. For example, an effective amount of an Rsk inhibitor is an amount of the inhibitor sufficient to suppress Rsk activity in a serine/threonine kinase assay.

As used herein, a "functional" molecule is a molecule in a form in which it exhibits a property by which it is characterized. By way of example, a functional enzyme is one which exhibits the characteristic catalytic activity by which the enzyme is characterized.

The term "inhibit," as used herein, refers to the ability of a compound of the invention to reduce or impede a described function. Preferably, inhibition is by at least 10%, more preferably by at least 25%, even more preferably by at least 50%, and most preferably, the function is inhibited by at least 75%.

The phrase "inhibit cancer cell growth", as used herein, refers to both direct and indirect inhibition of growth, regardless of the mechanism. For example, inhibiting a cancer cell from adhering to another cell or substrate can inhibit growth indirectly, when adhesion is required for the cell to proliferate.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

As used herein, the term "pharmaceutically acceptable carrier" includes any of the standard pharmaceutical carriers, such as a phosphate buffered saline solution, water and emulsions such as an oil/water or water/oil emulsion, and various types of wetting agents.

As used herein, the term "purified" and the like terms relate to the isolation of a molecule or compound in a form that is substantially free (at least 60% free, preferably 75% free, and most preferably 90% free) from other components normally associated with the molecule or compound in a native environment.

The term "standard," as used herein, refers to something used for comparison. For example, a standard can be a known standard agent or compound which is administered or added to a control sample and used for comparing results when measuring said compound in a test sample. Standard can also refer to an "internal standard," such as an agent or compound which is added at known amounts to a sample and is useful in determining such things as purification or recovery rates when a sample is processed or subjected to purification or extraction procedures before a marker of interest is measured.

A "subject" of analysis, diagnosis, or treatment is an animal. Such animals include mammals, preferably a human.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

The general chemical terms used in the description of the compounds of the present invention have their usual meanings. For example, the term "alkyl" by itself or as part of another substituent means a straight or branched aliphatic chain having the stated number of carbon atoms.

The term "halo" includes bromo, chloro, fluoro, and iodo.

The term "haloalkyl" as used herein refers to a alkyl radical bearing at least one halogen substituent, for example, chloromethyl, fluoroethyl or trifluoromethyl and the like.

The term "C1-Cn alkyl" wherein n is an integer, as used herein, refers to a branched or linear alkyl group having from one to the specified number of carbon atoms. Typically, C1-C6 alkyl groups include, but are not limited to, methyl, ethyl, n-propyl, iso-propyl, butyl, iso-butyl, sec-butyl, tert-butyl, pentyl, hexyl and the like.

The term "C2-Cn alkenyl" wherein n is an integer, as used herein, represents an olefinically unsaturated branched or linear group having from 2 to the specified number of carbon atoms and at least one double bond. Examples of such groups include, but are not limited to, 1-propenyl, 2-propenyl, 1,3-butadienyl, 1-butenyl, hexenyl, pentenyl, and the like.

The term "C2-Cn alkynyl" wherein n is an integer refers to an unsaturated branched or linear group having from 2 to the specified number of carbon atoms and at least one triple bond. Examples of such groups include, but are not limited to, 1-propynyl, 2-propynyl, 1-butynyl, 2-butynyl, 1-pentynyl, and the like.

As used herein, the term "optionally substituted" refers to zero to four substituents, wherein the substituents are each independently selected. More preferredly, the term refers to zero to three independently selected substituents.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. Aryl groups (including bicyclic aryl groups) can be unsubstituted or substituted with one, two, or three substituents independently selected from loweralkyl, haloalkyl, alkoxy, amino, alkylamino, dialkylamino, hydroxy, halo, and nitro. Substituted aryl includes aryl compounds having one or two C1-C6 alkyl, halo, or amino substituents. The term (alkyl)aryl refers to any aryl group which is attached to the parent moiety via the alkyl group.

The term "C3-Cn cycloalkyl" wherein n=4-8, represents cyclopropyl, cyclobutyl, cyclopentyl, cyclohexyl, cycloheptyl, and cyclooctyl.

The term "heterocyclic group" refers to a C3-C8 cycloalkyl group containing from one to three heteroatoms wherein the heteroatoms are selected from the group consisting of oxygen, sulfur, and nitrogen.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

The term, "parenteral" means not through the alimentary canal but by some other route such as subcutaneous, intramuscular, intraspinal, or intravenous.

As used herein, the term "treating" includes alleviating the symptoms associated with a specific disorder or condition and/or preventing or eliminating said symptoms.

As used herein, the term "RSK inhibitor" includes any compound or condition that specifically inhibits or reduces the kinase activity of RSK or which inhibits any function of RSK. Such inhibitory effects may result from directly, or indirectly, interfering with the protein's ability to phosphorylate its substrate, or may result from inhibiting the expression (transcription and/or translation) of RSK.

Processes for preparing compounds of formula I or for preparing intermediates useful for preparing compounds of formula I are provided as further embodiments of the invention. Intermediates useful for preparing compounds of formula I are also provided as further embodiments of the invention.

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Processes for preparing compounds of formula (I) are provided as further embodiments of the invention and are illustrated by the following procedures in which the meanings of the generic radicals are as given above unless otherwise qualified.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, -ketoglutarate, and -glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising an inhibitor identified in the invention and an instructional material which describes administering the inhibitor or a composition comprising the inhibitor to a cell or a subject. This should be construed to include other embodiments of kits that are known to those skilled in the art, such as a kit comprising a (preferably sterile) solvent suitable for dissolving or suspending the composition of the invention prior to administering the compound to a cell or a subject. Preferably the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention.

The invention is now described with reference to the following Examples and Embodiments. Without further description, it is believed that one of ordinary skill in the art can, using the preceding description and the following illustrative examples, make and utilize the present invention and practice the claimed methods. The following working examples therefore, are provided for the purpose of illustration only and specifically point out the preferred embodiments of the present invention, and are not to be construed as limiting in any way the remainder of the disclosure. Therefore, the examples should be construed to encompass any and all variations which become evident as a result of the teaching provided herein.

EXPERIMENTAL EXAMPLES

The short and convergent synthetic approach to 1 started with the preparation of flavonol 4, as outlined in Scheme 1.

Naringenin (4', 5,7-trihydroxyflavanone; see Scheme 1) was treated with benzyl bromide and excess $K_2CO_3$, resulting in concomitant β-elimination and benzyl protection to give the chalcone 2 in 81% yield. Formation of the desired flavanone 3 was accomplished in good yields (70-80%) using catalytic $I_2$ in DMSO at 140° C.[6] Introduction of a 3-OH group was achieved using DMDO,[7] followed by opening of the formed epoxide with catalytic p-toluenesulfonic acid to afford flavonol 4 in 78% yield.[8]

Preparation of the carbohydrate moiety is outlined in Scheme 2. Compound 5 was synthesized from L-rhamnose by known methods.[9]

Because O-3 and O-4 of 1 are both acetylated, while O-2 is unprotected, an appropriate orthogonal protecting group for O-2 was sought. Accordingly, using a procedure reported by Crich and co-workers,[10] regioselective protection of the O-3 and O-4 hydroxyl groups was achieved using 2,3-butanedione and trimethylorthoformate to give 6 in 89% yield. Benzyl protection of O-2 proceeded in 85% yield via the agency of NaH and benzyl bromide in THF to give the fully protected rhamnose. Benzylation of this OH group was chosen to allow for a mild and efficient global deprotection at the end of the synthesis. Removal of the O-3,4 protecting group was accomplished using TFA-$H_2O$ in $CH_2Cl_2$ to afford 7 in 93% yield. Bis-acetylation of 7 with $Ac_2O$, $NEt_3$ and catalytic 4-dimethylaminopyridine (DMAP) gave 2-O-benzyl-3,4-di-O-acetylrhamnose derivative 8 in yields exceeding 90%. Conversion to the rhamnosyl bromide 9 was accomplished in 84% yield by treatment with $Br_2$ in $CH_2Cl_2$ at 0° C.

Condensation of 4 and 9 in the presence of $Ag_2O$ provided perbenzylated SL101-1(10), exclusively as the α-anomer, in 60% yield (Scheme 3). Other commonly used glycosylation methods[11] such as benzyltriethylamine bromide and dilute aqueous KOH failed. Global debenzylation using Pearlman's catalyst (Pd(OH)$_2$/C) in the presence of $H_2$ gave SL0101-1 (1) in 94% yield. The synthetic compound had spectral data in full agreement with the authentic, naturally derived sample.

In conclusion, a short and efficient approach to the naturally occurring p90 Rsk inhibitor 1 has been completed. This convergent approach has permitted access to 1 on a preparative scale and should provide facile access to structurally related analogues.

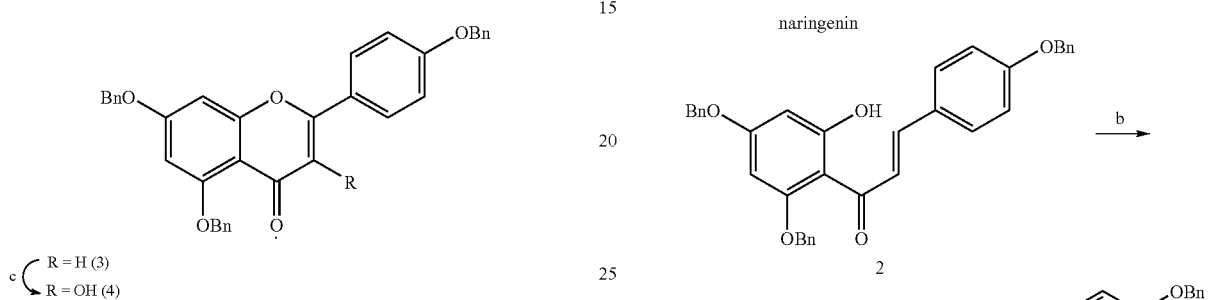

*Conditions: (a) BnBr, $K_2CO_3$, acetone, reflux, (81%); (b) cat. 12, DMSO, 140° C., (72%); (c) DMDO, acetone, $CH_2Cl_2$, 0° C. then pTsOH, $CHCl_3$, (78%).

-continued

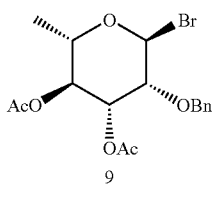

9

<sup>a</sup>Conditions: (a) 2,3 butanedione, CH(OMe)$_3$, cat. CSA, MeOH, reflux, (89%); (b) BnBr, NaH, THF, reflux, (85%); (c) TFA:H$_2$O (20:2), CH$_2$Cl$_2$, (93%); (d) Ac$_2$O, NEt$_3$, cat. DMAP, CH$_2$Cl$_2$, (100%); (e) Br$_2$, CH$_2$Cl$_2$, 0° C., (84%).

Scheme 3

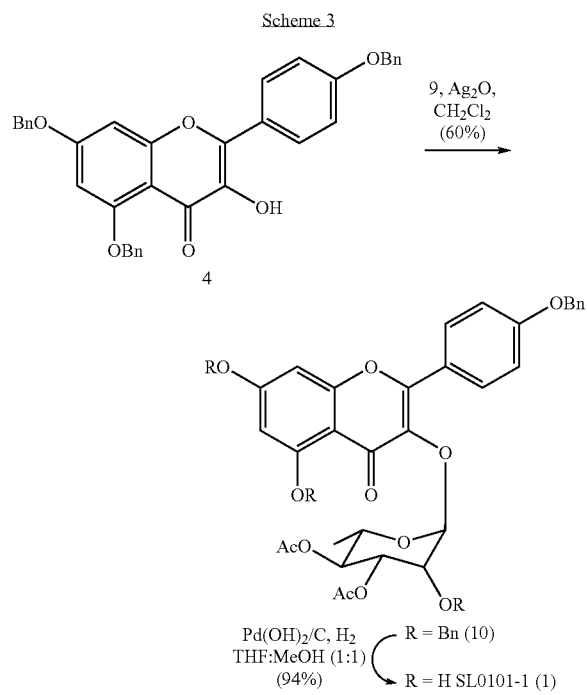

General Methods

Reagents and solvents were reagent grade and used without further purification. Methylene chloride was distilled from calcium hydride, and toluene was distilled from sodium. Anhydrous grade THF and Et$_2$O were purchased from VWR. All reactions involving air or moisture sensitive reagents or intermediates were performed under a nitrogen or argon atmosphere. Flash chromatography was performed using Silicycle 40-60 mesh silica gel. Analytical TLC was performed using 0.25 mm EM silica gel 60 F$_{250}$ plates that were visualized by irradiation (254 nm) or by staining with Hanessian's stain (cerium molybdate).

Optical rotations were obtained using a Jasco digital polarimeter. $^1$H and $^{13}$C NMR spectra were obtained using 300 MHz and 500 MHz Varian instruments. Chemical shifts are reported in parts per million (ppm δ) referenced to the residual $^1$H resonance of the solvent (CDCl$_3$, 7.26 ppm; DMSO-d$_6$, 2.49 ppm). $^{13}$C spectra were referenced to the residual $^{13}$C resonance of the solvent (CDCl$_3$, 77.3 ppm; DMSO-d$_6$, 39.5 ppm). Splitting patterns are designated as follows: s, singlet; br, broad; d, doublet; dd, doublet of doublets; t, triplet; q, quartet; m, mulitplet. High resolution mass spectra were obtained at the Michigan State University-NIH Mass Spectrometry Facility. Melting points were determined for all crystalline compounds and are uncorrected.

Experimental Procedures

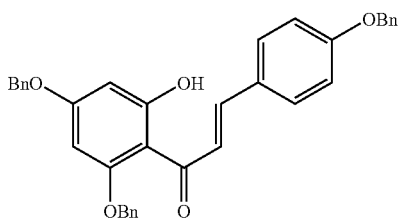

E-3-(4-Benzyloxyphenyl)-1-(2,4-bisbenzyloxy-6-hydroxyphenyl)propanone (2). To a solution containing 5.00 g (18.4 mmol) of 4',5,7-trihydroxyflavanone in 150 mL of acetone was added 10.0 g (7.00 mL, 57.0 mmol) of BnBr followed by 15.4 g (110 mmol) of K$_2$CO$_3$. The reaction mixture was heated at reflux overnight under N$_2$. The cooled reaction mixture was then concentrated under diminished pressure. The residue was redissolved in 300 mL of ethyl acetate, washed with three 100-mL portions of H$_2$O, dried (MgSO$_4$) and concentrated under diminished pressure. The residue was purified by flash chromatography on a silica gel column (28×4 cm).

Elution with 3:1 hexanes-ethyl acetate gave 2 as a bright yellow solid: yield 8.07 g (81%); mp 127-129° C.; silica gel TLC R$_f$ 0.53 (3:1 hexanes-ethyl acetate); $^1$H NMR (CDCl$_3$) δ 5.02 (s, 2H), 5.07 (s, 4H), 6.17 (dd, 2H, J=17.4, 2.1 Hz), 6.76 (d, 2H, J=8.4 Hz), 6.97 (d, 2H, J=8.7 Hz), 7.32 (m, 15H), 7.74 (dd, 2H, J=15.3, 14.7 Hz) and 14.81 (br s, 1H); $^{13}$C NMR (CDCl$_3$) δ 70.3, 70.5, 71.6, 92.7, 95.3, 106.5, 115.2, 125.4, 127.5, 127.7, 127.9, 128.3, 128.4, 128.6, 128.8, 128.9, 129.1, 129.2, 130.4, 135.7, 136.1, 136.8, 143.0, 160.5, 161.9, 165.3, 169.1 and 192.8; mass spectrum (FAB), m/z 543.2177 (M+H)$^+$ (C$_{36}$H$_{31}$O$_5$ requires 543.2171).

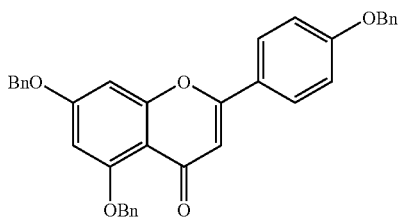

5,7-Bis-(benzyloxy)-2-(4-(benzyloxy)phenyl)-4H-chromen-4-one (3). To a solution containing 7.50 g (13.8 mmol) of 2 in 50 mL of DMSO was added 0.39 g (1.52 mmol) of I$_2$. The reaction mixture was heated at reflux overnight under N$_2$. The cooled reaction mixture was diluted with 200 mL of ethyl acetate and washed with two 100-mL portions of 1N HCl. The organic layer was separated, dried (MgSO$_4$) and concentrated under diminished pressure. The residue was purified by flash chromatography on a silica gel column (28×4 cm). Elution with 1:1 hexanes-ethyl acetate gave 3 as an off-white solid: yield 5.50 g (72%); mp 60-62° C.; silica gel TLC R$_f$ 0.19 (2:1 hexanes-ethyl acetate); $^1$H NMR (CDCl$_3$) δ 5.10 (s, 2H), 5.12 (s, 2H), 5.22 (s, 2H), 6.48 (d, 1H, J=2.5 Hz), 6.63 (d, 1H, J=2.0 Hz), 7.05 (d, 2H, J=8.5 Hz), 7.37-7.46 (m, 15H), 7.64 (d, 2H, J=8.0 Hz) and 7.80 (d, 2H, J=9.0 Hz); $^{13}$C NMR (CDCl$_3$) δ 70.4, 70.7, 70.9, 74.9, 94.4, 98.6, 107.9, 110.0, 115.5, 118.2, 124.2, 126.8, 127.6, 127.7, 127.9, 128.5, 128.6, 128.7, 128.8, 128.9, 129.0, 135.9, 136.5, 136.7, 159.9, 160.9, 161.4, 163.1 and 171.6; mass spectrum (FAB), m/z 541.2019 (M+H)$^+$ (C$_{36}$H$_{29}$O$_5$ requires 541.2015).

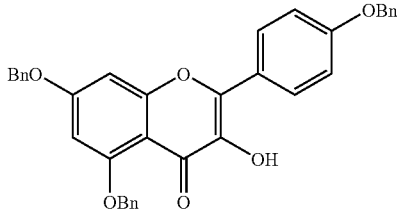

5,7-Bis-(benzyloxy)-2-(4-(benzyloxy)phenyl)-3-hydroxy-4H-chromen-4-one (4). To a solution containing 1.00 g (1.85 mmol) of 3 in 30 mL of CH$_2$Cl$_2$ at 0° C. was added 30 mL of a 0.9-0.11 M solution of DMDO in acetone. The reaction mixture was stirred at 0° C. overnight under N$_2$.

The solvent was concentrated under diminished pressure, and then the residue was redissolved in 50 mL of CH$_2$Cl$_2$ and treated with catalytic pTsOH. The reaction mixture was stirred at 0° C. for 30 min. The solvent was concentrated under diminished pressure and the residue was purified by flash chromatography on a silica gel column (25×4 cm).

Elution with 1:1 hexanes-ethyl acetate gave 4 as a light brown solid: yield 0.63 g (78% based on consumed starting material) and 0.22 g of unreacted starting material; silica gel TLC R$_f$ 0.28 (3:1 hexanes-ethyl acetate); $^1$H NMR (DMSO-d$_6$) δ 5.19 (s, 2H), 5.25 (s, 2), 6.69 (s, 1H), 6.97 (br s, 1H), 7.18 (d, 2H, J=8.5 Hz), 7.30-7.44 (m, 11H), 7.46-7.50 (m, 2H), 7.67 (d, 2H, J=7.5 Hz), 8.14 (d, 2H, J=8.5 Hz) and 9.15 (s, 1H); $^{13}$C NMR (DMSO-d$_6$) δ 70.1, 70.5, 70.7, 94.6, 98.0, 102.2, 107.4, 115.6, 127.2, 128.1, 128.5, 128.6, 128.7, 128.87, 128.92, 129.16, 129.23, 129.4, 136.8, 137.4, 137.6, 138.8, 142.5, 158.7, 159.5, 159.8, 163.4 and 171.9; mass spectrum (FAB), m/z 557.1967 (M+H)$^+$ (C$_{36}$H$_{29}$O$_6$ requires 557.1964).

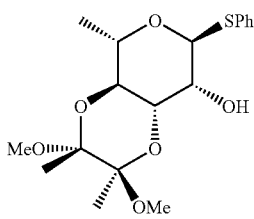

Phenyl 3,4-O-(2,3-Dimethoxybutan-2,3-diyl)-1-thio-α-L-rhamnopyranoside (6). A solution containing 3.80 g (14.8 mmol) of 5, 1.40 g (1.42 mL, 16.3 mmol) of 2,3-butanedione, 4.72 g (4.87 mL, 44.5 mmol) of trimethylorthoformate, and 0.52 g (2.22 mmol) 10-camphorsulfonic acid in 100 mL of MeOH was heated at reflux overnight. The cooled reaction mixture was neutralized with NEt$_3$ and concentrated under diminished pressure. The residue was purified by flash chromatography on a silica gel column (28×4 cm). Elution with 6:1 hexanes-ethyl acetate gave 6 as a colorless foam: yield 4.87 g (89%); silica gel TLC R$_f$ 0.19 (3:1 hexanes-ethyl acetate); $[α]_D^{23}$ −290.9 (c 1.36, CHCl$_3$); $^1$H NMR (CDCl$_3$) δ 1.26 (d, 3H, J=6.3 Hz), 1.31 (s, 3H), 1.33 (s, 3H), 3.24 (s, 3H), 3.31 (s, 3H), 3.78 (m, 1H), 3.98 (dd, 1H, J=10.2, 3.0 Hz), 4.18 (dd, 1H, J=3.0, 1.2 Hz), 4.26 (m, 1H), 5.49 (s, 1H), 7.26-7.32 (m, 3H) and 7.42-7.47 (m, 2H); $^{13}$C NMR (CDCl$_3$) δ 16.7, 17.9, 18.0, 47.9, 48.3, 68.0, 68.8, 69.0, 71.6, 88.1, 100.1, 100.5, 127.5, 129.2, 131.6 and 134.5; mass spectrum (FAB), m/z 370.1448 (M)$^+$ (C$_{18}$H$_{26}$O$_6$S requires 370.1450).

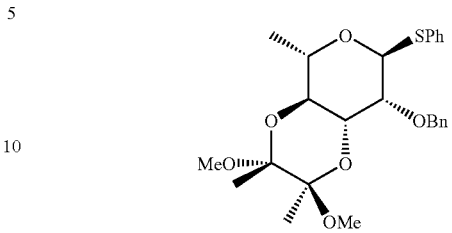

Phenyl 2-O-Benzyl-3,4-O-(2,3-dimethoxybutan-2,3-diyl)-1-thio-α-L-rhamnopyranoside. To a solution containing 4.80 g (13.0 mmol) of 6 in 100 mL of anhydrous THF at 0° C. was added slowly 1.03 g (25.9 mmol) of a 60% dispersion of NaH. After stirring for 5 min, the reaction mixture was removed from the ice bath and 3.33 g (2.31 mL, 19.5 mmol) of BnBr was added. The reaction mixture was heated at reflux overnight under N$_2$. The reaction mixture was then quenched by the slow dropwise addition of sat. aqueous NH$_4$Cl, diluted with 200 mL of H$_2$O, and extracted with three 150-mL portions of ethyl acetate. The combined organic layer was dried (MgSO$_4$) and concentrated under diminished pressure.

The residue was purified by flash chromatography on a silica gel column (28×4 cm). Elution with 4:1 hexanes-ethyl acetate gave the product as a colorless foam: yield 5.05 g (85%); silica gel TLC R$_f$ 0.62 (3:1 hexanes-ethyl acetate); $[α]_D^{21}$ −206.7 (c 1.08, CHCl$_3$); $^1$H NMR(CD)Cl$_3$) δ 1.29 (d, 3H, J=6.3 Hz), 1.34 (s, 3H), 1.36 (s, 3H), 3.29 (s, 3H), 3.31 (s, 3H), 3.95 (m, 3H), 4.26 (m, 1H), 4.71 (m, 1H), 4.90 (d, 1H, J=12.0 Hz), 5.45 (d, 1H, J=0.6 Hz) and 7.25-7.45 (m, 10H); $^{13}$C NMR (CDCl$_3$) δ 16.8, 18.0, 18.1, 47.9, 48.1, 68.4, 69.1, 69.6, 73.2, 77.9, 87.5, 99.8, 100.0, 127.3, 127.7, 128.1, 128.4, 129.2, 131.3, 135.0 and 138.6; mass spectrum (FAB), m/z 460.1919 (M)$^+$ (C$_{25}$H$_{32}$O$_6$S requires 460.1920).

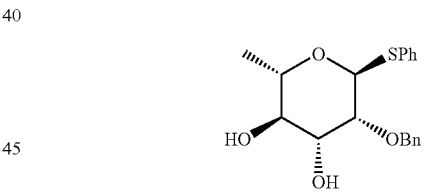

Phenyl 2-O-Benzyl-1-thio-α-L-rhamnopyranoside (7). To a solution containing 5.00 g (10.87 mmol) of phenyl 2-O-benzyl-3,4-O-(2,3-dimethoxybutan-2,3-diyl)-1-thio-α-L-rhamnopyranoside in 100 mL of CH$_2$Cl$_2$ was added 22 mL of 10:1 TFA-H$_2$O. The reaction mixture was stirred at room temperature for 40 min, quenched cautiously with sat. aq NaHCO$_3$, and diluted with 75 mL of CH$_2$Cl$_2$. The organic layer was separated, washed with two 100-mL portions of brine, dried (MgSO$_4$) and concentrated under diminished pressure. The residue was purified by flash chromatography on a silica gel column (28×4 cm).

Elution with 1:1 hexanes-ethyl acetate gave 7 as a colorless solid: yield 3.50 g (93%); silica gel TLC R$_f$ 0.47 (1:1 hexanes-ethyl acetate); $[OG]_D^{21}$ −92.1 (c 1.00, CHCl$_3$); $^1$H NMR (CDCl$_3$) δ 1.34 (d, 3H, J=6.0 Hz), 2.42 (br s, 2H), 3.52 (t, 1H, J=9.5 Hz), 3.76 (dd, 1H, J=9.0, 3.5 Hz), 4.01 (dd, 1H, J=3.5, 1.5 Hz), 4.13 (m, 1H), 4.49 (d, 1H, J=11.5 Hz), 4.75 (d, 1H, J=12.0 Hz), 5.60 (s, 1H), 7.29 (m, 8H) and 7.47 (m, 2H); $^{13}$C NMR (CDCl$_3$) δ 17.9, 69.3, 72.3, 72.6, 74.5, 79.8, 85.2, 127.7, 128.2, 128.4, 128.9, 129.3, 131.8, 134.4 and 137.3; mass spectrum (FAB), m/z 346.1237 (M)+ ($C_{19}H_{22}O_4S$ requires 346.1239).

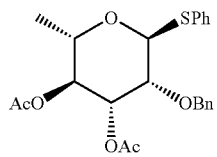

Phenyl 3,4-Di-O-acetyl-2-O-benzyl-1-thio-α-L-rhamnopyranoside (8). A solution containing 3.45 g (9.97 mmol) of 7, 4.07 g (3.77 mL, 39.9 mmol) of $Ac_2O$, 5.03 g (6.78 mL, 49.9 mmol) of $NEt_3$, and 0.13 g (0.10 mmol) of 4-(N,N-dimethyl)aminopyridine in 75 mL of anhyd $CH_2Cl_2$ was stirred at room temperature overnight under $N_2$. The reaction mixture was then diluted with 100 mL of $CH_2Cl_2$ and washed with two 100-mL portions of $H_2O$. The organic layer was separated, dried ($MgSO_4$) and concentrated under diminished pressure. The residue was purified by flash chromatography on a silica gel (25×4 cm).

Elution with 2:1 hexanes-ethyl acetate gave 8 as a colorless solid: yield 4.30 g (100%); silica gel TLC $R_f$ 0.51 (2:1 hexanes-ethyl acetate); $[\alpha]_D^{21}$ −43.3 (c 1.56, $CHCl_3$); $^1H$ NMR ($CDCl_3$) δ 1.24 (d, 3H, J=6.0 Hz), 1.99 (s, 3H), 2.07 (s, 2H), 4.08 (dd, 1H, J=3.5, 1.5 Hz), 4.28 (m, 1H), 4.54 (d, 1H, J=12.5 Hz), 4.68 (d, 1H, J=12.0 Hz), 5.16 (dd, 1H, J=10.0, 3.5 Hz), 5.27 (t, 1H, J=9.5 Hz), 5.50 (d, 1H, J=2.0 Hz), 7.27-7.33 (m, 8H) and 7.44 (m, 2H); $^{13}C$ NMR ($CDCl_3$) δ 17.7, 21.1, 68.0, 71.6, 71.7, 72.8, 77.2, 85.6, 127.7, 128.2, 128.2, 128.7, 129.4, 131.6, 134.3, 137.6, 170.2 and 170.5; mass spectrum (FAB), m/z 431.1530 (M+H)+ ($C_{23}H_{27}O_6S$ requires 431.1528).

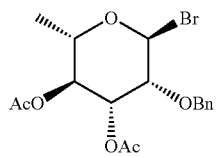

3,4-Di-O-acetyl-2-O-benzyl-α-L-rhamnopyranosyl Bromide (9). To a solution containing 1.00 g (2.32 mmol) of 8 in 25 mL of anhydrous $CH_2Cl_2$ at 0° C. under argon was added 0.50 g (0.16 mL, 3.14 mmol) of $Br_2$. The reaction mixture was stirred at 0° C. for 1 h. The reaction mixture was diluted with 20 mL of $CH_2Cl_2$ and washed with 100 mL of 3% aq $NaHSO_3$. The organic layer was separated, dried ($MgSO_4$) and concentrated under diminished pressure. The residue was then purified by flash chromatography on a silica gel column (26×4 cm).

Elution with 2:1 hexanes-ethyl acetate gave 9 as a colorless oil: yield 0.78 g (84%); silica gel TLC $R_f$ 0.21 (2:1 hexanes-ethyl acetate); $^1H$ NMR ($CDCl_3$) δ 1.26 (d, 3H, J=6.0 Hz), 1.99 (s, 3H), 2.07 (s, 3H), 4.03 (m, 1H), 4.10 (m, 1H), 4.66 (dd, 2H, J=15.0, 12.0 Hz), 5.23 (t, 1H, J=10.2 Hz), 5.54 (dd, 1H, J=10.2, 3.3 Hz), 6.34 (s, 1H) and 7.35 (m, 5H); $^{13}C$ NMR ($CDCl_3$) δ 17.3, 21.0, 70.0, 70.8, 71.4, 73.5, 79.2, 86.5, 128.2, 128.8, 137.4, 169.9 and 170.2. Note: must be used immediately; product decomposes rather rapidly (1-2 days).

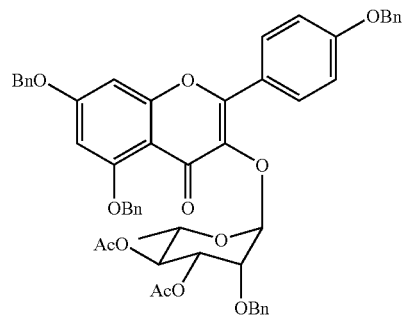

5,7-Bis-(benzyloxy)-2-(4-(benzyloxy)phenyl)-3-[3,4-di-O-acetyl-2-O-benzyl-α-L-rhamnopyranosyloxy]-4H-chromen-4-one (10). To a stirred suspension containing 0.28 g (0.51 mmol) of 4, 0.24 g (1.02 mmol) of freshly prepared $Ag_2O$ and 4 Å molecular sieves in 10 mL of $CH_2Cl_2$ was added 0.41 g (1.02 mmol) of 9 in 5 mL of $CH_2Cl_2$. The reaction mixture was stirred at room temperature for 4 h, then diluted with 20 mL of $CH_2Cl_2$ and filtered through a Celite pad and washed with $CH_2Cl_2$. The filtrate was concentrated under diminished pressure and the residue was purified by flash chromatography on a silica gel column (25×3 cm).

Elution with 3:1 hexanes-ethyl acetate gave 10 as a colorless solid: yield 0.27 g (60%); silica gel TLC $R_f$ 0.37 (2:1 hexanes-ethyl acetate); $[\alpha]_D^{23}$ −84.3 (c 0.06, $CHCl_3$); $^1H$ NMR ($CDCl_3$) δ 0.87 (d, 3H, J=6.0 Hz), 1.95 (s, 3H), 1.99 (s, 3H), 3.39-3.48 (m, 1H), 4.42 (m, 1H), 4.74 (dd, 2H, J=30.9, 12.3 Hz), 5.09 (s, 2H), 5.14 (s, 2H), 5.16 (m, 1H), 5.26 (s, 2H), 5.30 (m, 2H), 5.74 (s, 1H), 6.49 (d, 2H, J=25.5 Hz), 7.14 (d, 2H, J=8.7 Hz), 7.25-7.47 (m, 20H), 7.63 (d, 2H, J=7.8 Hz) and 7.84 (d, 2H, J=8.4 Hz); $^{13}C$ NMR ($CDCl_3$) δ 17.0, 20.7, 68.1, 70.0, 70.36, 70.42, 70.6, 71.0, 72.5, 75.5, 93.8, 98.1, 98.7, 109.9, 114.6, 123.1, 126.5, 127.2, 127.5, 127.6, 128.1, 128.3, 128.5, 128.6, 128.6, 130.4, 135.5, 136.2, 137.7, 137.9, 154.1, 158.8, 159.7, 160.3, 162.7, 169.7, 170.0 and 173.0; mass spectrum (FAB), m/z 877.3221 (M+H)+ ($C_{53}H_{49}O_{12}$ requires 877.3224).

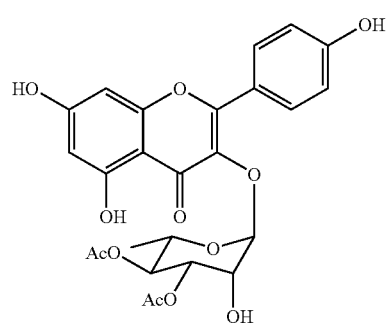

SL0101-1 (1). A suspension containing 0.26 g (0.29 mmol) of 10 and 0.10 g of $Pd(OH)_2/C$ in 10 mL of 1:1 THF-MeOH was purged with $H_2$ and maintained under a $H_2$ atmosphere for 1 h. The reaction mixture was then diluted with ethyl acetate, filtered through a Celite pad and washed with ethyl acetate. The filtrate was concentrated under diminished pressure to give 1 as a tan solid: yield 0.14 g (94%); silica gel TLC $R_f$ 0.35 (1:1:0.1 hexanes-ethyl acetate-methanol); $[\alpha]_D^{17}$ −106.5 (c 0.65, MeOH); $^1H$ NMR (acetone-$d_6$) δ 0.86 (d, 3H, J=6.3 Hz), 1.32 (br s, 1H), 2.01 (s, 3H), 2.06 (s, 3H), 3.54 (m, 1H), 4.48 (d, 1H, J=2.1 Hz), 5.12 (m, 1H), 5.23 (dd, 1H, J=9.9, 2.7 Hz), 5.61 (d, 1H, J=0.9 Hz), 6.32 (brs, 1H), 6.53 (brs, 1H), 7.09 (d, 2H, J=8.4 Hz), 7.90 (d, 2H, J=8.1 Hz), 9.44 (br s, 2H) and 12.62 (br s, 1H); $^{13}$C NMR (acetone-d$_6$) δ 17.0, 20.2, 68.7, 70.5, 71.7, 94.1, 99.2, 101.5, 105.2, 115.9, 121.8, 131.1, 134.8, 157.5, 158.0, 160.5, 162.7, 164.6, 169.7, 170.1 and 178.5; mass spectrum (FAB), m/z 517.1345 (M+H)$^+$ ($C_{25}H_{25}O_{12}$ requires 517.1346).

Methods for Testing the Activity of Compounds of the Invention

Methods for testing the ability of SL0101(SL0101-1, SL0101-2, and SL1010-3), and analogs and derivatives thereof, synthesized according to the methods disclosed herein, to inhibit p90 ribosomal S6 kinase (RSK), are known to those of ordinary skill in the art. Some specific assays are provided in citation number 5 (Smith et al., Cancer Res., 2005, 65:1027), which is incorporated by reference in its entirety.

The structure of compounds SL0101-1, -2, and -3 and their ability to inhibit the kinase activity of p90 RSK are provided in Table 1.

TABLE 1

| | $R_1$ | $R_2$ | $R_3$ | $IC_{50}$ |
|---|---|---|---|---|
| SL0101-1(1) | OH | OAc | OAc | 89 nM |
| SL0101-2 | OH | OH | OAc | 189 nM |
| SL0101-3 | OAc | OH | OAc | 580 nM |

The invention should not be construed to be limited solely to the assays and methods described herein, but should be construed to include other methods and assays as well. Other methods which were used but not described herein are well known and within the competence of one of ordinary skill in the art of chemistry, biochemistry, molecular biology, and clinical medicine. One of skill in the art will know that other assays and methods are available to perform the procedures described herein.

The abbreviations used herein have their conventional meaning within the clinical, chemical, and biological arts. In the case of any inconsistencies, the present disclosure, including any definitions therein will prevail.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. Accordingly, the present invention is not intended to be limited to the embodiments shown herein but is to be accorded the widest scope consistent with the principles and novel features disclosed herein.

BIBLIOGRAPHY (1) (a) Bang, Y.-J.; Kwon, J.-H.; Kang, S.-H.; Kim, J.-W.; Yang, Y.-C. *Biochem. Biophys. Res. Commun.* 1998, 250, 43. (b) Schmidt, C. M.; McKillop, I. A.; Cahil, P. A.; Sitzmann, J. V. 1997, 236, 54. (c) Janes, P. W.; Daly, R. J.; deFazio, A.; Sutherland, R. L. *Oncogene.* 1994, 9, 3601. (d) Kurokawa, H.; Lenferink, A. E.; Simpson, J. F.; Pisacane, P. L.; Sliwkowski, M. X.; Forbes, J. T.; Arteaga, C. L. *Cancer Res.* 2000, 60, 5887.

(2) (a) Lewis, T. S.; Shapiro, P. S.; Ahn, N. G. *Adv. Cancer. Res.* 1998, 74, 49. (b) Cobb, M. H. *Prog. Biophys. Mol. Biol.* 1999, 71, 479. (c) Kolch, W. *Biochem. J.* 2000, 351, 289.

(3) (a) Yntema, H. G.; van den Helm, B.; Kissing, J.; van Dujinhove, G.; Poppelaars, F.; Chelly, J.; Moraine, C.; Fryns, J. P.; Hamel, B. C., Helbronner, H.; Pander, H. J.; Brunner, H. G.; Ropers, H. K.; Cremers, F. P.; van Bokhoven, H. *Genomics* 1999, 62, 332.

(4) Nebreda, A. R.; Gavin, A. C. *Science.* 1999, 286, 1309.

(5) Smith, J. A.; Poteet-Smith, C. E.; Xu, Y.; Errington, T. M.; Hecht, S. M.; Lannigan, D. A. *Cancer Res.,* 2005, 65:3: 1027-1034.

(6) (a) Kitagawa, M.; Yamamoto, K.; Katakura, S.; Kanno, H.; Yamada, K. *Chem. Pharm. Bull.* 1991, 39, 2681. (b) Khan, M. S. Y.; Sharma, P. *Indian J. Chem. Sect. B.* 1993, 32, 817.

(7) (a) Adam, W.; Hadijiarapoglou, L.; Smerz, A. *Chem. Ber.* 1991, 124, 227. (b) Adam, W.; Chan, Y.-Y.; Cremer, D.; Scheutzow, D.; Schindler, M. *J. Org. Chem.* 1987, 52, 2800. (c) Murray, R. W.; Jeyaraman, R. *J. Org. Chem.* 1987, 50, 3890.

(8) (a) Adam, W.; Golsch, D.; Hadjiarapoglou, L. *J. Org. Chem.* 1991, 56, 7292. (b) Lee, Y.-J.; Wu, T.-D. *J Chin. Chem. Soc.* 2001, 48, 201.

(9) (a) Groneberg, R. D.; Miyazaki, T.; Stylianides, N. A.; Schulze, T. J.; Stahl, W.; Schreiner, E. P.; Suzuki, T.; Iwabuchi, Y.; Smtih, A. L.; Nicolaou, K. C. *J. Am. Chem. Soc.* 1993, 115, 7593. (b) Pozsgay, V. *Carbohydr. Res.* 1992, 235, 1992. (c) Bashir, N. B.; Phythian, S. J.; Reason, A. J.; Roberts, S. M. *J. Chem. Soc. Perkin Trans.* 11995, 2203.

(10) Crich, D.; Vinod, A. U.; Picione, J. *J. Org. Chem.* 2003, 68, 8453.

(11) Demetzos, C.; Skaltsounis, A. L.; Tillequin, F.; Koch, M. *Carbohydr. Res.* 1990, 207, 131.

What is claimed is:

1. A method for synthesizing a compound having the general structure of formula I:

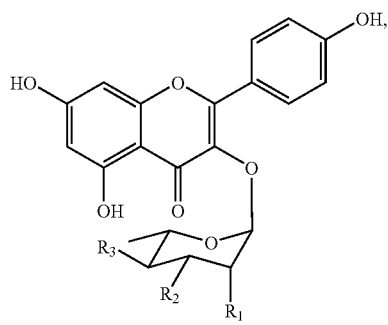

wherein $R_1$ and $R_2$ are each independently selected from the group consisting of OH and OAc, and $R_3$ is OAc;

said method comprising;

synthesizing from naringenin a flavonol (4)

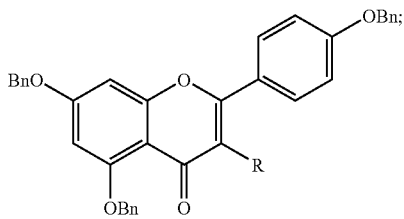

wherein the conditions for step $c_1$ comprise TFA:H$_2$O (20:2), CH$_2$Cl$_2$, (93%);

synthesizing a carbohydrate moiety by synthesizing from L-rhamnose compound 5

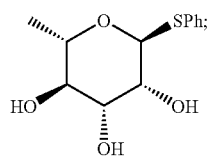

synthesizing rhamnosyl bromide from compound 5, and then condensing 4 and the rhamnosyl bromide.

2. The method of claim 1, said method comprising synthetic schemes 1, 2, and 3;

wherein synthetic scheme 1 comprises the following steps;

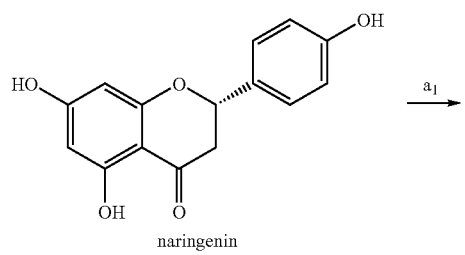

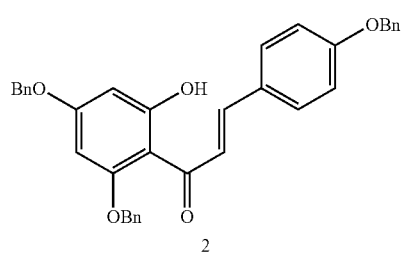

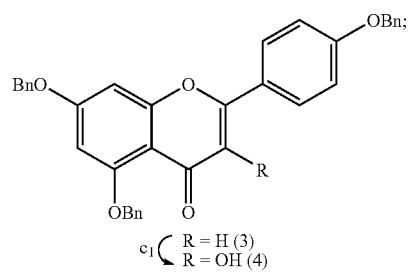

wherein the conditions for step $a_1$ comprise BnBr, K$_2$CO$_3$, acetone, reflux, (81%), wherein the conditions for step $b_1$ comprise cat. I$_2$, DMSO, 140° C., (72%), wherein the conditions for step $c_1$ comprise DMDO, acetone, CH$_2$Cl$_2$, 0° C., then pTsOH, CHCl$_3$, (78%);

wherein synthetic scheme 2 comprises the following steps;

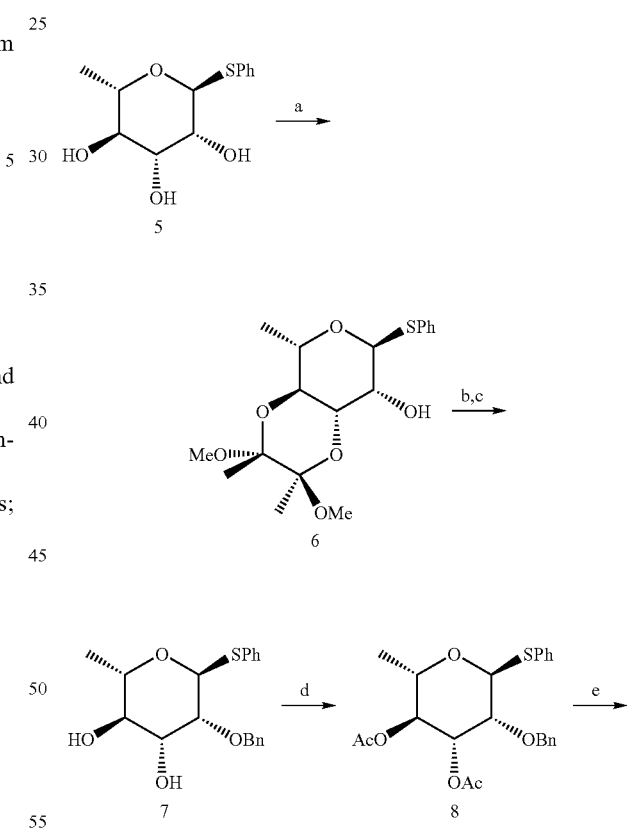

wherein the conditions for step a comprise 2,3 butanedione, CH(OMe)$_3$, cat. CSA, MeOH, reflux, (89%);

wherein the conditions for step b comprise BnBr, NaH, THF, reflux, (85%);

wherein the conditions for step c comprise TFA:H$_2$O (20:2), CH$_2$Cl$_2$, (93%);

wherein the condition for step d comprise Ac$_2$O, NEt$_3$, cat. DMAP, CH$_2$Cl$_2$, (100%);

wherein the conditions for step e comprise Br$_2$, CH$_2$Cl$_2$, 0° C., (84%); and wherein synthetic scheme 3 comprises the following steps;

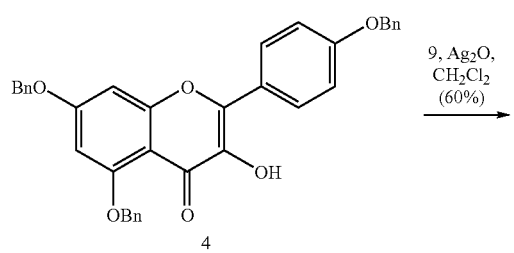

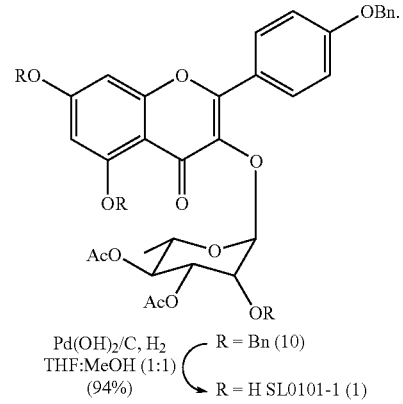

3. The method of claim 1, further wherein said compound has 90 kDa ribosomal S6 kinase inhibitory activity.

4. The method of claim 3, wherein R$_1$ is OH and R$_2$ is OAc.

5. The method of claim 3, wherein R$_1$ is OH and R$_2$ is OH.

6. The method of claim 3, wherein R$_1$ is OAc and R$_2$ is OH.

* * * * *

UNITED STATES PATENT AND TRADEMARK OFFICE
CERTIFICATE OF CORRECTION

PATENT NO. : 7,605,241 B2 Page 1 of 1
APPLICATION NO. : 11/794969
DATED : October 20, 2009
INVENTOR(S) : Sidney H. Hecht and David J. Maloney It is certified that error appears in the above-identified patent and that said Letters Patent is hereby corrected as shown below:

At Column 1, Line 15, please replace the paragraph entitled "REFERENCE TO GOVERNMENT GRANT" with the following paragraph:

This invention was supported in part by NIH Research Grant Calif. 50771. The U.S. Government has certain rights in this invention.

Signed and Sealed this

Thirtieth Day of March, 2010

David J. Kappos
*Director of the United States Patent and Trademark Office*